United States Patent
Wang et al.

(10) Patent No.: US 11,434,235 B2
(45) Date of Patent: Sep. 6, 2022

(54) SOLID FORM OF DIHYDROPYRIMIDINE COMPOUND AND PREPARATION METHOD THEREFOR AND USE THEREOF

(71) Applicant: SICHUAN KELUN-BIOTECH BIOPHARMACEUTICAL CO., LTD., Chengdu (CN)

(72) Inventors: Tianming Wang, Chengdu (CN); Chengxi Yang, Chengdu (CN); Jiaqiang Cai, Chengdu (CN); Wei Liu, Chengdu (CN); Baolei Zhang, Chengdu (CN); Qiang Tian, Chengdu (CN); Shuai Song, Chengdu (CN); Hao Hu, Chengdu (CN); Weibiao Han, Chengdu (CN); Youqiang Li, Chengdu (CN); Xing Chen, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 138 days.

(21) Appl. No.: 16/981,430

(22) PCT Filed: May 6, 2019

(86) PCT No.: PCT/CN2019/085641
§ 371 (c)(1),
(2) Date: Sep. 16, 2020

(87) PCT Pub. No.: WO2019/218883
PCT Pub. Date: Nov. 21, 2019

(65) Prior Publication Data
US 2021/0024514 A1 Jan. 28, 2021

(30) Foreign Application Priority Data

May 16, 2018 (CN) .......................... 201810468685.0

(51) Int. Cl.
C07D 417/14 (2006.01)
A61K 45/06 (2006.01)
(52) U.S. Cl.
CPC ............ C07D 417/14 (2013.01); *A61K 45/06* (2013.01); *C07B 2200/13* (2013.01)
(58) Field of Classification Search
CPC .................................................. C07D 417/14
See application file for complete search history.

(56) References Cited

U.S. PATENT DOCUMENTS

2016/0206616 A1  7/2016  Zhang et al.

FOREIGN PATENT DOCUMENTS

| CN | 104672222 A | 6/2015 |
|---|---|---|
| CN | 104945395 A | 9/2015 |
| CN | 107400125 B | 11/2017 |
| CN | 108329308 A | 7/2018 |
| WO | 2015078391 A1 | 6/2015 |
| WO | 2015144093 A1 | 10/2015 |
| WO | 2017/198201 A1 | 11/2017 |
| WO | 2018090862 A1 | 5/2018 |

OTHER PUBLICATIONS

Caira; Crystalline Polymorphism of Organic Compounds; Topics in Current Chemistry; 1998; vol. 198, pp. 163-208.
European Patent Office; Extended European Search Report of EP Application No. 19804104.8; dated Jul. 9, 2021.
Deres et al., Inhibition of Hepatitis B Virus Replication by Drug-Induced Depletion of Nucleocapsids, Science, vol. 299, No. 5608, Feb. 7, 2003, pp. 893-896.
Hacker et al., Antivirals Interacting with Hepatitis B Virus Core Protein and Core Mutations May Misdirect Capsid Assembly in a Similar Fashion, Biochemical Pharmacology, vol. 66, No. 12, Dec. 15, 2003, pp. 2273-2279.
Stray et al., A Heteroaryldihydropyrimidine Activates and Can Misdirect Hepatitis B Virus Capsid Assembly, Proceedings of the National Academy of Sciences, vol. 102, No. 23, Jun. 7, 2005, pp. 8138-8143.
Wu, et al., Preclinical Characterization of GLS4, an Inhibitor of Hepatitis B Virus Core Particle Assembly, Antimicrobial Agents and Chemotherapy, vol. 57, No. 11, Nov. 2013, pp. 5344-5354.
ISA/CN; International Search Report and Written Opinion for PCT/CN2019/085641; dated Jul. 25, 2019, 13 pages.
European Patent Office; Communication Pursuant to Article 94(3) EPC; EP Application No. 19804104-8-1110; dated Feb. 23, 2022; 4 pgs.
The State Intellectual Property Office of People's Republic of China; First Office Action; CN Application No. 201810468685.0; 11 pgs.
Chinese Application No. 201810468685.0, Office Action dated Jun. 29, 2022, 8 pages (5 pages English Translation and 3 pages Original).

*Primary Examiner* — Yong S. Chong
(74) *Attorney, Agent, or Firm* — Kilpatrick Townsend & Stockton LLP

(57) ABSTRACT

Disclosed are a solid form of (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl) acrylic acid, a preparation method therefor, a pharmaceutical composition comprising same, and the use thereof in the preparation of drugs for preventing or treating viral diseases.

9 Claims, 4 Drawing Sheets

SOLID FORM OF DIHYDROPYRIMIDINE COMPOUND AND PREPARATION METHOD THEREFOR AND USE THEREOF

CROSS-REFERENCE TO RELATED APPLICATIONS

The present application is a 371 National Phase application of PCT/CN2019/085641, filed May 6, 2019, which application claims priority to CN 201810468685.0, filed May 16, 2018, the disclosures of which are hereby incorporated by reference in their entireties for all purposes.

FIELD OF THE INVENTION

The present invention relates to a solid form of (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)acrylic acid (hereinafter referred to as "the compound of Formula (I)"), a method for preparing the solid form, a pharmaceutical composition comprising the solid form, and the use of the solid form for the prevention or treatment of viral diseases including, but not limited to, viral hepatitis type A, viral hepatitis type B, viral hepatitis type C, influenza, herpes and acquired immunodeficiency syndrome (AIDS).

BACKGROUND OF THE INVENTION

Hepatitis type B virus (HBV) is a common hepatophilic DNA viral pathogen. The virus may result in acute hepatitis, chronic hepatitis, hepatic fibrosis, liver cirrhosis, liver cancer and the like.

Drugs for treating hepatitis type B include interferon and nucleoside analogues (such as lamivudine and adefovir dipivoxil). Among them, interferon interacts with a cell surface receptor to enable cells to produce antiviral proteins, thereby inhibiting the replication of hepatitis B virus. Disadvantages thereof are a relatively low effective response rate and need for long-term injection administration. The nucleoside analogues take effects mainly by inhibiting replication of viral polymerase (reverse transcriptase). The disadvantage thereof is that the drugs need long lasting application which often results in viral mutation and leads to drug resistance.

Further, viral hepatitis type B can be treated with non-nucleoside analogues. A heteroaryl dihydropyrimidine compound (Bay41-4109) discovered by Deres et al. may prevent HBV virus replication by inhibiting viral capsid protein assembly (Science, 2003, 299, 893-896). The specific mechanism of action is as follows: the dihydropyrimidine compound induces defective assembly of core proteins, resulting in formation of unstable capsid proteins and acceleration of the degradation of the core proteins (*Biochem. Pharmacol.*, 2003, 66, 2273-2279). Heteroaryl dihydropyrimidine compound HAP1 discovered by Zlotnick et al. (*Proc. Natl. Acad. Sci.*, 2005, 102, 8138-8143) and a heteroaryl dihydropyrimidine compound (GLS4) reported by SUNSHINE LAKE PHARMA CO., LTD. (*Antimicrob. Agents Chemother.*, 2013, 57, 5344-5354; WO2015078391, US2016206616 and WO2015144093) also have anti-HBV activity.

Although the above compounds exhibit some degree of viral suppression, the antiviral activity thereof is still not satisfied. Moreover, some compounds also exhibit significant toxic effects (e.g., GLS4 exhibits significant hERG cardiotoxicity).

The compound of Formula (I) recently developed not only exhibits a potent antiviral effect, but also has no cardiotoxicity and possesses good pharmacokinetic properties, which are advantageous for the improvement in the therapeutic effect on viral diseases:

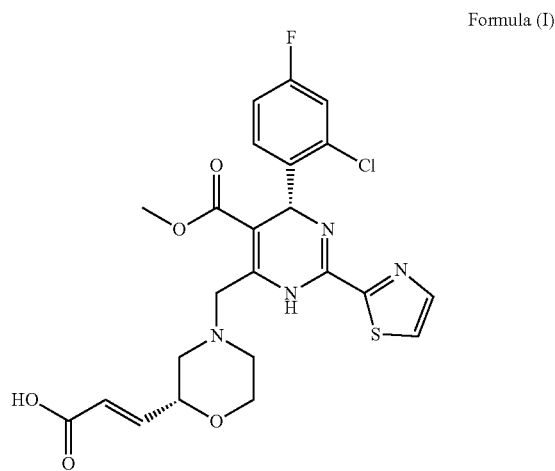 [SMILES: COC(=O)C1=C(CN2CCO[C@H](/C=C/C(=O)O)C2)NC(c2nccs2)=N[C@H]1c1ccc(F)cc1Cl]

Formula (I)

Different crystalline forms of a same drug may vary significantly in respect of the stability and bioavailability, thus affecting the efficacy of the drug. As such, it is of great significance to develop a stable crystalline form of a compound which is more advantageous for use in drug processing and pharmaceutical compositions, and provides more qualitative and quantitative information for the therapeutic effect study of the solid drug. This is also an urgent need in the drug development.

SUMMARY OF THE INVENTION

The present invention provides solid forms of the compound of Formula (I), the chemical name of which is (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)acrylic acid:

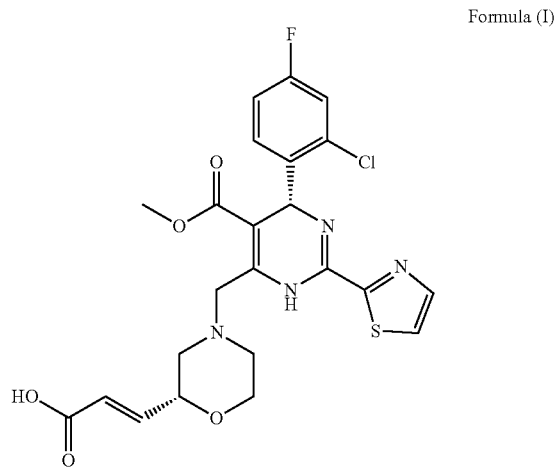 [SMILES: COC(=O)C1=C(CN2CCO[C@H](/C=C/C(=O)O)C2)NC(c2nccs2)=N[C@H]1c1ccc(F)cc1Cl]

Formula (I)

An aspect of the present invention provides crystalline form A of the compound of Formula (I), characterized in that the X-ray powder diffraction (XRPD) pattern of the crystalline form A has characteristic peaks at diffraction angles (2θ) of 8.7±0.2, 17.5±0.2°, 19.3±0.2°, 20.3±0.2° and 21.4±0.2°.

Another aspect of the present invention provides a method for the preparation of the crystalline form A or amorphous form of the present invention.

Another aspect of the present invention provides a pharmaceutical composition comprising the crystalline form A and/or amorphous form of the present invention, and one or more pharmaceutically acceptable carriers or one or more additional therapeutic agents.

Another aspect of the present invention provides a pharmaceutical formulation comprising the crystalline form A and/or amorphous form of the present invention, and one or more pharmaceutically acceptable carriers.

Another aspect of the present invention provides use of the crystalline form A and/or amorphous form of the present invention, the pharmaceutical composition of the present invention, and/or the pharmaceutical formulation of the present invention in the manufacture of a medicament for preventing or treating a viral disease.

Another aspect of the present invention provides the crystalline form A and/or amorphous form of the present invention, the pharmaceutical composition of the present invention, and/or the pharmaceutical formulation of the present invention for use in the prevention or treatment of a viral disease.

Another aspect of the present invention provides a method for the prevention or treatment of a viral disease, comprising administering to a subject in need thereof an effective amount of the crystalline form A and/or amorphous form of the present invention, the pharmaceutical composition of the present invention and/or the pharmaceutical formulation of the present invention.

DETAILED DESCRIPTION OF THE INVENTION

Definitions

Unless otherwise defined in the context, all the technical and scientific terms used herein are intended to have the same meaning as commonly understood by a person skilled in the art. References to techniques employed herein are intended to refer to the techniques as commonly understood in the art, including those variations on techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps, though the additional unrecited elements or method steps are not necessarily present (i.e., these terms also contemplate the terms "substantially consisting of" and "consisting of").

The word "about" as used herein refers to, as appreciated by a person skilled in the art, a range within the acceptable standard error of a value, such as ±0.05, ±0.1, ±0.2, ±0.3, ±0.5, ±1, ±2 or ±3, etc.

The term "solid form" as used herein includes all solid forms of the compound of Formula (I), such as a crystalline form or amorphous form.

The term "amorphous" as used herein refers to any solid substance which lacks order in three dimensions. In some instances, amorphous solids can be characterized by known techniques, including XRPD crystal diffraction analysis, solid state nuclear magnet resonance (ssNMR) spectral analysis, differential scanning calorimetry (DSC), or some combination of these techniques. As illustrated below, an amorphous solid gives an XRPD pattern with no clear diffraction characteristic peaks.

The term "crystalline form" or "crystal" as used herein refers to any solid substance exhibiting three-dimensional order, which in contrast to an amorphous solid substance, gives a distinctive XRPD pattern with sharply defined peaks.

The term "X-ray powder diffraction pattern (XRPD pattern)" as used herein refers to the experimentally observed diffractogram or parameters, data or values derived therefrom. XRPD patterns are usually characterized by peak positions (abscissa) and peak intensities (ordinate).

The term "2θ" as used herein refers to the peak position in degrees (°) based on the setup of the X-ray diffraction experiment and is generally the unit on abscissa in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific crystalline form is intended to mean the 2θ values (in degrees) as measured using the X-ray diffraction experimental conditions as described herein.

The term "differential scanning calorimetry (DSC) graph" as used herein refers to a curve recorded on a differential scanning calorimeter.

The term "thermogravimetric analysis (TGA) graph" as used herein refers to a curve recorded on a thermogravimetric analyzer.

As used herein, the term "essentially the same" means that typical peak position and/or intensity variability are taken into account. For example, for X-ray diffraction peaks, one skilled in the art will appreciate that the peak positions (2θ) will show some variability, typically as much as 0.1 to 0.2 degree, and the apparatus for measuring the diffraction may also lead to some variability. Further, one skilled in the art will appreciate that relative peak intensities will vary due to difference between apparatuses as well as degree of crystallinity, preferred orientation, prepared sample surface, and other factors known to those skilled in the art.

Crystalline Form and Preparation Method

In some embodiments, the present invention provides crystalline form A of the compound of Formula (I), characterized in that the X-ray powder diffraction pattern of the crystalline form A has characteristic peaks at diffraction angles of 8.70±0.2°, 17.5±0.2°, 19.3±0.2°, 20.3±0.2° and 21.4±0.2°, Formula (I)

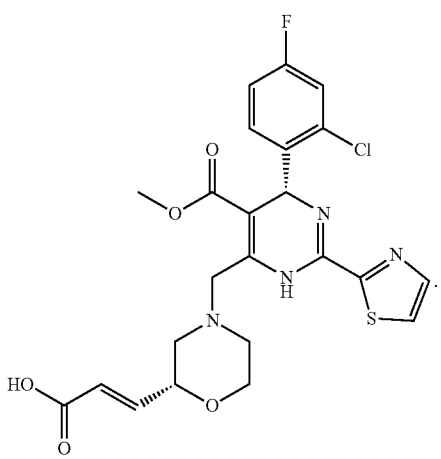

In preferred embodiments, the XRPD pattern of the crystalline form A of the compound of Formula (I) comprises characteristic peaks at diffraction angles (2θ) of 8.7±0.2°, 16.0±0.2°, 17.5±0.2°, 17.8±0.2°, 19.3±0.2°, 20.3±0.2°, 21.4±0.2°, 22.3±0.2° and 23.1±0.2°.

In more preferred embodiments, the XRPD pattern of the crystalline form A of the compound of Formula (I) comprises characteristic peaks at diffraction angles (2θ) of 8.7±0.2°, 10.8±0.2°, 15.8±0.2°, 16.0±0.2°, 17.5±0.2°, 17.80±0.2°, 19.30±0.2°, 19.5±0.2°, 20.3±0.2°, 21.1±0.2°, 21.4±0.2°, 22.3±0.2°, 23.1±0.2° and 27.0±0.2°.

In particularly preferred embodiments, the XRPD pattern of the crystalline form A of the compound of Formula (I) comprises characteristic peaks at the following diffraction angles (2θ), wherein the error range of the 2θ value is ±0.2°:

| 2θ (°) ± 0.2° | Interplanar spacing d (Å) | Intensity % |
| --- | --- | --- |
| 7.3 | 12.1 | 11.4 |
| 8.7 | 10.1 | 52.5 |
| 9.4 | 9.4 | 7.5 |
| 9.7 | 9.2 | 5.8 |
| 10.5 | 8.4 | 4.9 |
| 10.8 | 8.2 | 16.0 |
| 13.2 | 6.7 | 0.8 |
| 14.2 | 6.2 | 8.9 |
| 14.5 | 6.1 | 6.3 |
| 15.8 | 5.6 | 16.0 |
| 16.1 | 5.5 | 26.8 |
| 16.7 | 5.3 | 6.5 |
| 17.5 | 5.1 | 37.5 |
| 17.9 | 5.0 | 35.8 |
| 19.3 | 4.6 | 40.0 |
| 19.5 | 4.5 | 16.1 |
| 20.3 | 4.4 | 36.8 |
| 20.7 | 4.3 | 4.9 |
| 21.1 | 4.2 | 16.1 |
| 21.4 | 4.1 | 100.0 |
| 22.3 | 4.0 | 29.8 |
| 22.8 | 3.9 | 12.8 |
| 23.1 | 3.9 | 23.9 |
| 23.8 | 3.7 | 7.3 |
| 24.0 | 3.7 | 4.7 |
| 24.6 | 3.6 | 0.3 |
| 25.1 | 3.5 | 1.8 |
| 25.9 | 3.4 | 3.2 |
| 26.6 | 3.4 | 7.8 |
| 27.0 | 3.3 | 14.6 |
| 27.4 | 3.3 | 8.9 |
| 28.2 | 3.2 | 4.7 |
| 28.5 | 3.1 | 3.1 |
| 28.9 | 3.1 | 1.3 |
| 29.6 | 3.0 | 1.6 |
| 29.6 | 3.0 | 2.8 |
| 29.9 | 3.0 | 2.4 |
| 30.3 | 2.9 | 2.7 |
| 31.0 | 2.9 | 0.9 |
| 31.6 | 2.8 | 2.0 |
| 31.9 | 2.8 | 4.2 |
| 32.5 | 2.8 | 1.2 |
| 33.0 | 2.7 | 2.3 |
| 34.0 | 2.6 | 2.3 |
| 34.3 | 2.6 | 1.4 |

In more preferred embodiments, the XRPD pattern of the crystalline form A of the compound of Formula (I) comprises peaks at diffraction angles (2θ) essentially the same as shown in FIG. 1. In most preferred embodiments, the XRPD pattern of the crystalline form A of the compound of Formula (I) is as shown in FIG. 1.

In some embodiments, the endothermic peak in the differential scanning calorimetry (DSC) graph of the crystalline form A of the compound of Formula (I) appears at 173±2° C.

In more preferred embodiments, the DSC graph of the crystalline form A is as shown in FIG. 2.

In some embodiments, the crystalline form A of the compound of Formula (I) starts to decompose at 190±2° C. according to the thermogravimetric analysis (TGA) graph.

In preferred embodiments, the TGA graph of the crystalline form A is as shown in FIG. 3.

Another aspect of the present invention provides a method for the preparation of the crystalline form A of the compound of Formula (I) as mentioned above, and the method includes, but is not limited to, a slow volatilization method, a suspension stirring method, an permeation method, or a recrystallization method.

Among them, the solvent employed in the method is selected from the group consisting of methanol, ethanol, n-propanol, isopropanol, n-butanol, acetone, butanone, ethyl acetate, butyl acetate, isopropyl acetate, dimethyl carbonate, tetrahydrofuran, dichloromethane, chloroform, methyl tert-butyl ether, acetonitrile, anisole, toluene, diethyl ether, water, isopropyl ether, n-hexane, n-heptane, cyclohexane, and petroleum ether.

In some embodiments of the present invention, the crystalline form A is prepared by the slow volatilization method, which comprises the following steps: dissolving the compound of Formula (I) in a first suitable solvent to form a clear solution, then allowing it to stand at room temperature, volatilizing and removing the solvent, and collecting the solid to obtain the crystalline form A;

wherein the first suitable solvent is one or more of those selected from the group consisting of methanol, ethanol, n-propanol, isopropanol, n-butanol, acetone, butanone, ethyl acetate, butyl acetate, isopropyl acetate, dimethyl carbonate, tetrahydrofuran, dichloromethane, chloroform, methyl tert-butyl ether, acetonitrile, anisole, toluene, and diethyl ether; and the solvent is used in an amount allowing the formation of a clear solution of the compound of Formula (I).

Preferably, the weight/volume ratio (mg/ml) of the compound of Formula (I) to the first suitable solvent is 100:1 to 10:1.

Alternatively, the first suitable solvent is a mixed solvent of solvent A and solvent B, wherein the solvent A is one or more of those selected from the group consisting of acetone, tetrahydrofuran, ethyl acetate, acetonitrile, toluene, dichloromethane, water, and methyl tert-butyl ether; and the solvent B is one or more of those selected from the group consisting of methanol, acetone, tetrahydrofuran, ethyl acetate, acetonitrile, toluene, and dichloromethane;

preferably, the volume ratio of the solvent A to the solvent B is 1:2-2:1; and preferably, the volume ratio of the solvent A to the solvent B is 1:1;

preferably, the solvent A or the solvent B is used in an amount allowing complete dissolution of the compound of Formula (I).

In some embodiments of the present invention, the crystalline form A is prepared by the slow volatilization method, which comprises the following steps: dissolving the compound of Formula (I) in solvent A to form a clear solution, adding solvent B to mix, and then allowing it to stand at room temperature, volatilizing and removing the solvent, and collecting the solid to obtain the crystalline form A; preferably, the solvent A is one or more of those selected from the group consisting of methanol, acetone, tetrahydrofuran, ethyl acetate, acetonitrile, toluene, dichloromethane, water, and methyl tert-butyl ether; and the solvent B is one or more of those selected from the group consisting of methanol, acetone, tetrahydrofuran, ethyl acetate, acetonitrile, toluene, dichloromethane, and water;

preferably, the volume ratio of the solvent A to the solvent B is 1:2-2:1; and preferably, the volume ratio of the solvent A to the solvent B is 1:1.

In other embodiments of the present invention, the crystalline form A is prepared by the recrystallization method, which comprises the following steps: heating and stirring the compound of Formula (I) in a second suitable solvent to form a clear solution, slowly cooling it to room temperature followed by filtration, and collecting the solid to obtain the crystalline form A;

preferably, the second suitable solvent is selected from the group consisting of isopropanol, acetonitrile, toluene, and n-propanol; preferably, the weight/volume ratio (g/ml) of the compound of Formula (I) to the solvent is 1:(5-10);

alternatively, the second suitable solvent is diethyl ether, and the weight/volume ratio (g/ml) of the compound of Formula (I) to diethyl ether is 1:60.

In other embodiments of the present invention, the crystalline form A is prepared by the suspension stirring method, which comprises the following steps: dispersing and suspending the compound of Formula (I) or an amorphous form thereof in a third suitable solvent, then stirring the suspension at room temperature or under a high temperature condition, and collecting the solid to obtain the crystalline form A; preferably, the third suitable solvent is one or more of those selected from the group consisting of ethanol, n-propanol, n-butanol, diethyl ether, isopropyl ether, acetonitrile, toluene, n-hexane, n-heptane, cyclohexane, methyl tert-butyl ether, water and petroleum ether; preferably, the third suitable solvent is used in an amount allowing the solute to suspend therein (the weight/volume ratio (mg/ml) of the solute to the solvent is preferably 150:1 to 10:1); preferably, the high temperature condition is 60° C.

In other embodiments of the present invention, the crystalline form A is prepared by the permeation method, which comprises the following steps: placing the compound of Formula (I) in container A, placing the open container A in container B which contains a suitable amount of a fourth suitable solvent, sealing container B, allowing it to stand at room temperature, and collecting the solid to obtain the crystalline form A;

preferably, the fourth suitable solvent is one or more of those selected from the group consisting of methanol, etha-nol, isopropyl acetate, n-hexane, acetonitrile, diethyl ether, methyl tert-butyl ether, and toluene; preferably, the standing time is no less than 8 days.

Another aspect of the present invention provides an amorphous form of the compound of Formula (I), and the XRPD pattern of the amorphous form comprises no significant sharp diffraction peaks.

In preferred embodiments, the XRPD pattern of the amorphous form is as shown in FIG. 4.

Another aspect of the present invention provides a method for the preparation of an amorphous form of the compound of Formula (I), and the method comprises the following steps: dissolving the compound of Formula (I) in a fifth suitable solvent to form a clear solution, which is rotary evaporated under reduced pressure to obtain the amorphous form;

preferably, the fifth suitable solvent is one or more of those selected from the group consisting of dichloromethane and chloroform;

preferably, the water bath temperature is 40-50° C., and more preferably 45° C.

In another aspect, the compound of Formula (I) of the present invention and an organic or inorganic acid can form a corresponding salt of the compound of Formula (I), including, but not limited to: fumarate, citrate, tartrate, phosphate, maleate, succinate, adipate, sulfate, hydrochloride, carbonate, phosphate, hydrobromide, nitrate, malate, glycolate, mucate, lactate, gentisate, methanesulfonate, camphorsulfonate, benzenesulfonate, p-toluenesulfonate, ethanedisulfonate, naphthalenedisulfonate, hippurate, nicotinate, oxalate, malonate, L-arginine, lysine;

wherein the molar ratio of the compound of Formula (I) to the organic acid or inorganic acid is preferably 1:1 or 2:1 or 3:1.

On the other hand, the compound of Formula (I) of the present invention and an organic base or an inorganic base can form a corresponding salt of the compound of Formula (I).

Preferably, the salt formed by the compound of Formula (I) and an inorganic base includes, but is not limited to, ammonium salt, magnesium salt, potassium salt, sodium salt, calcium salt, lithium salt, and the like;

alternatively, the organic base is selected from the group consisting of meglumine, benzylamine, betaine, dimethylethanolamine, diethylaminoethanol, tromethamine, diethanolamine, ethylenediamine, imidazole, piperazine, tromethamine, triethylamine, choline, and the like;

wherein the molar ratio of the compound of Formula (I) to the organic base or inorganic base is preferably 1:1 or 2:1 or 3:1.

Pharmaceutical Composition and Therapeutic Method

Another aspect of the present invention provides a pharmaceutical composition comprising the crystalline form A and/or the amorphous form of the compound of Formula (I), and one or more pharmaceutically acceptable carriers or one or more additional therapeutic agents.

The "additional therapeutic agent" refers to an additional pharmacologically active substance other than the crystalline form A and/or amorphous form of the compound of Formula (I) of the present invention, e.g., an additional antiviral agent which can achieve a synergistic therapeutic effect with the compound of Formula (I).

Another aspect of the present invention provides a pharmaceutical formulation comprising the crystalline form A and/or the amorphous form of the compound of Formula (I) of the present invention, and one or more pharmaceutically acceptable carriers.

The "pharmaceutically acceptable carrier" refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutical formulation of the present invention can act systemically and/or topically. To this end, it can be administered through a suitable route, such as through injection, intravenous, intraarterial, subcutaneous, intraperitoneal, intramuscular, or transdermal administration, or administered via oral, buccal, nasal, transmucosal, topical, as an ophthalmic formulation, or via inhalation.

For these routes of administration, the formulation of the present invention can be administered in a suitable dosage form.

The dosage form may be solid, semi-solid, liquid, or gas formulations, including, but not limited to, tablets, capsules, powders, granules, lozenges, hard candies, powders, sprays, creams, salves, suppositories, gels, pastes, lotions, ointments, aqueous suspensions, injectable solutions, suspensions, elixirs, and syrups.

The pharmaceutical formulation of the present invention may be manufactured by any process well known in the art, e.g., by means of mixing, dissolving, granulating, dragee-making, levigating, emulsifying, lyophilizing processes, or the like.

The amount or dosage of the compound of the present invention in the pharmaceutical formulation may be about 0.01 mg to about 1000 mg, suitably 0.1-500 mg, preferably 0.5-300 mg, etc.

Another aspect of the present invention provides use of the crystalline form A and/or the amorphous form of the compound of Formula (I), the pharmaceutical composition of the present invention and/or the pharmaceutical formulation of the present invention in the manufacture of a medicament for preventing or treating a viral disease, preferably, the viral disease includes, but is not limited to, viral hepatitis type A, viral hepatitis type B, viral hepatitis type C, influenza, herpes and acquired immunodeficiency syndrome (AIDS).

Another aspect of the present invention provides a method for the prevention or treatment of a viral disease, comprising administering to a subject in need thereof an effective amount of the crystalline form A, the amorphous form of the compound of Formula (I) of the present invention, the pharmaceutical composition of the present invention and/or the pharmaceutical formulation of the present invention. Preferably, the viral disease includes, but is not limited to, viral hepatitis type A, viral hepatitis type B, viral hepatitis type C, influenza, herpes and acquired immunodeficiency syndrome (AIDS).

Another aspect of the present invention provides the crystalline form A and/or the amorphous form of the compound of Formula (I), the pharmaceutical composition of the present invention or the pharmaceutical formulation of the present invention for use in the prevention or treatment of a viral disease. Preferably, the viral disease includes, but is not limited to, viral hepatitis type A, viral hepatitis type B, viral hepatitis type C, influenza, herpes and acquired immunodeficiency syndrome (AIDS).

The crystalline form of the compound of Formula (I) provided by the present invention not only has an excellent effect in preventing or treating a viral disease, but also exhibits good chemical stability, physical stability, and pharmacokinetic properties. For example, the crystalline form of the compound of Formula (I) of the present invention has good solubility, low hygroscopicity, etc., and thus is more advantageous for sufficient dissolution upon administration and preparation of a formulation thereof, and can retain adequate biological activity. Meanwhile, it has good high-temperature resistance, high-humidity resistance and fluidity, is more suitable and convenient for mass production and for forming a formulation, and can maintain the reliability during transportation and storage, thereby effectively ensuring the quality and safety of the drug. In addition, it further has good photostability, and does not require special packaging treatment to prevent the influence of light, thereby reducing costs. It does not degrade by the influence of light, thereby improving the safety of the drug and sustain the efficacy upon long-term storage.

EXAMPLES

The present invention is further illustrated with reference to the following examples, which are only used to illustrate the technical solutions of the present invention, and are not intended to limit the scope thereof, and those skilled in the art may make some non-essential improvements and adjustments, which still fall within the scope of the present invention.

Information on the test instruments and methods employed in the experiments:

X-ray powder diffraction (XRPD):

X'Pert3 Powder diffractometer using Cu target radiation was employed, and the detection was performed at room temperature with Absolute scan. The detection range was 3.5° to 40° with a step size of 0.013° and a dwell time of 50 s, scan time: 1.

The instrument for the differential scanning calorimetry (DSC) test was DSC1 (METTLER TOLEDO).

The instrument for the thermogravimetric analysis (TGA) test was METTLER TOLEDO.

Both DSC and TGA instruments had a heating rate of 10K/min.

The experimental conditions for the dynamic vapor sorption (DVS) were as follows:

The detection was performed with DVS Intrinsic (SMS) at 25° C. in a cycle-DMDT mode.

Example 1: Preparation of (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)acrylic acid (the compound of Formula (I))

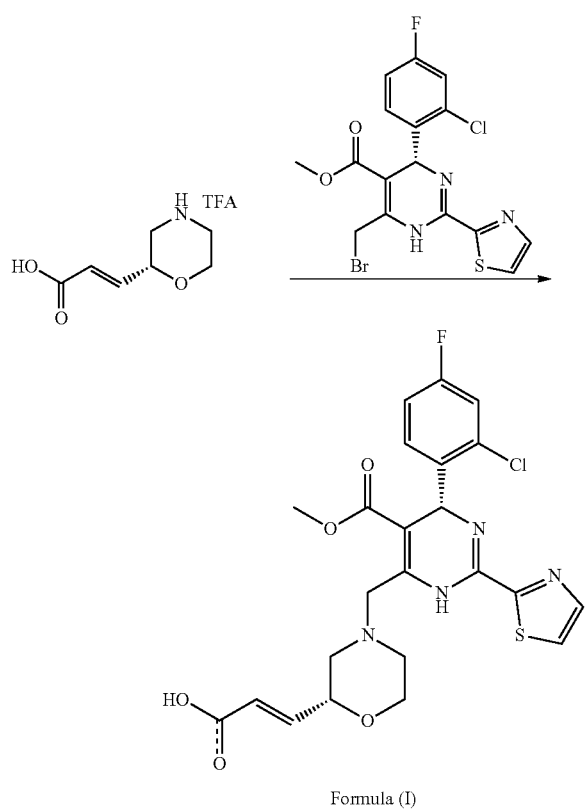

Formula (I)

Figure 7:
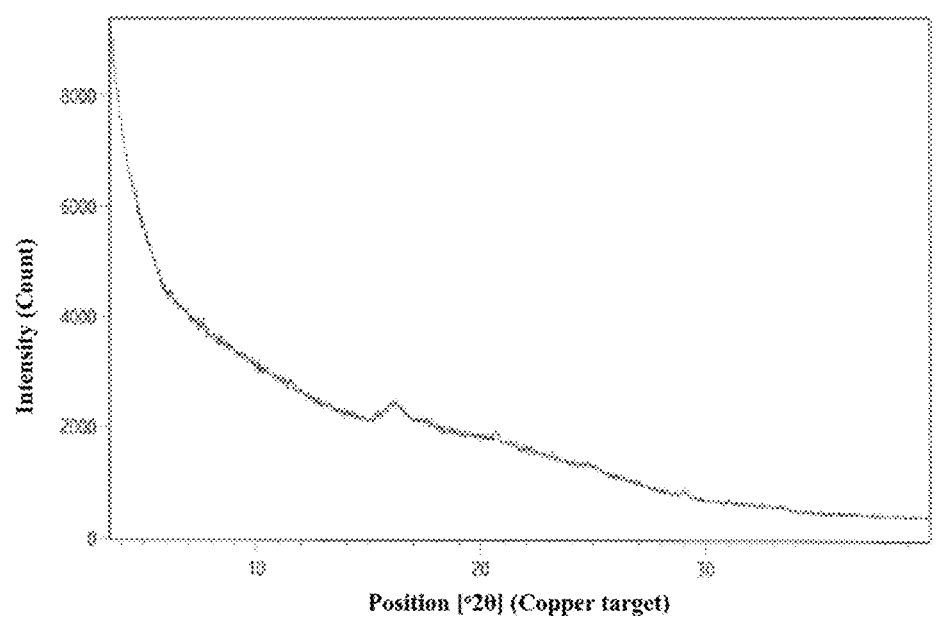
FIG. 7: an XRPD pattern of the compound of Formula (I) prepared in Example 1.

At room temperature, (R)-methyl 6-(bromomethyl)-4-(2-chloro-4-fluorophenyl)-2-(thiazol-2-yl)-1,4-dihydropyrimidine-5-carboxylate (400 mg, 0.90 mmol) and (R,E)-3-(morpholin-2-yl)acrylic acid trifluoroacetate salt (488 mg, 1.80 mmol) were dissolved in dichloromethane (10 mL), N,N-diisopropylethylamine (696 mg, 5.40 mmol) was added, and the reaction was performed at room temperature overnight. The reaction solution was concentrated to give a crude product, which was purified by preparative liquid chromatography, to afford the compound of Formula (I) (205 mg). The resulting sample was subjected to the XRPD analysis, and the XRPD pattern is shown in FIG. 7, which indicates that the obtained solid is an amorphous form of the compound of Formula (I).

Its structure was characterized as follows:

$^1$H NMR (400 MHz, DMSO-$d_6$) δ 12.44 (s, 1H), 9.68 (s, 1H), 7.98 (dd, J=27.6, 3.1 Hz, 2H), 7.48-7.36 (m, 2H), 7.18 (td, J=8.5, 2.6 Hz, 1H), 6.73 (dd, J=15.8, 4.1 Hz, 1H), 6.04 (s, 1H), 5.93 (dd, J=15.8, 1.6 Hz, 1H), 4.23 (d, J=9.3 Hz, 1H), 4.01-3.90 (m, 3H), 3.68 (t, J=10.2 Hz, 1H), 3.52 (s, 3H), 2.94 (d, J=11.0 Hz, 1H), 2.82 (d, J=11.1 Hz, 1H), 2.41 (dd, J=11.0, 8.6 Hz, 1H), 2.08 (t, J=10.7 Hz, 1H). ESI-MS (m/z): 521.1 [M+H]$^+$.

Example 2: Preparation of the Crystalline Form a of the Compound of Formula (I)

Figure 1:
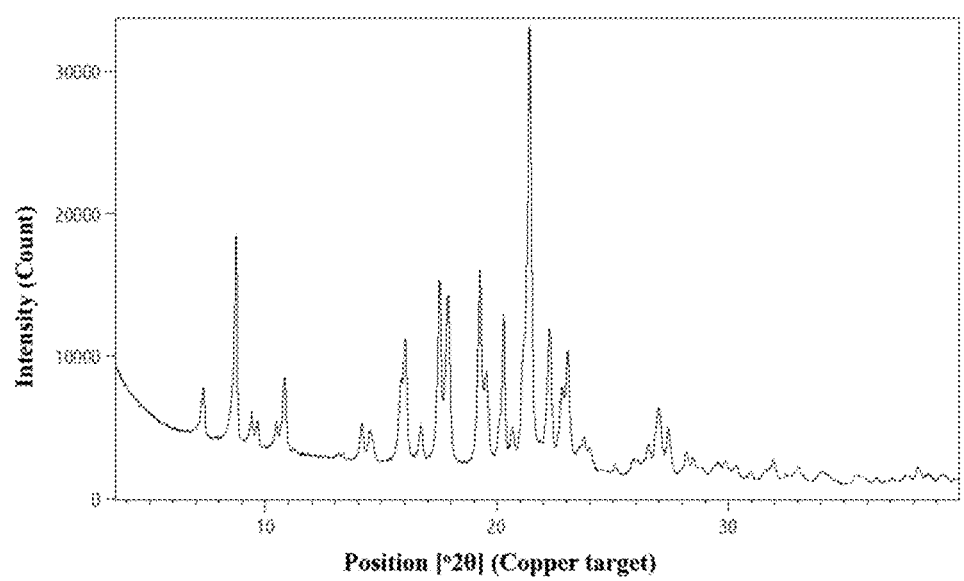
FIG. 1: an XRPD pattern of the crystalline form A of the compound of Formula (I).

30 mg of the compound of Formula (I) prepared in Example 1 was weighed and dissolved in 0.9 ml of methanol to form a clear solution, and then the solution was allowed to stand at room temperature. The solvent was volatilized and removed, leading to the crystallization. The solid was collected, and the resulting sample was subjected to XRPD detection. The XRPD pattern is as shown in FIG. 1, and the relevant data are shown in Table 1, indicating the crystalline form A of the compound of Formula (I) was obtained.

TABLE 1

| 2θ (°) ± 0.2° | Interplanar spacing d (Å) | Intensity % |
|---|---|---|
| 7.3 | 12.1 | 11.4 |
| 8.7 | 10.1 | 52.5 |
| 9.4 | 9.4 | 7.5 |
| 9.7 | 9.2 | 5.8 |
| 10.5 | 8.4 | 4.9 |
| 10.8 | 8.2 | 16.0 |
| 13.2 | 6.7 | 0.8 |
| 14.2 | 6.2 | 8.9 |
| 14.5 | 6.1 | 6.3 |
| 15.8 | 5.6 | 16.0 |
| 16.1 | 5.5 | 26.8 |
| 16.7 | 5.3 | 6.5 |
| 17.5 | 5.1 | 37.5 |
| 17.9 | 5.0 | 35.8 |
| 19.3 | 4.6 | 40.0 |
| 19.5 | 4.5 | 16.1 |
| 20.3 | 4.4 | 36.8 |
| 20.7 | 4.3 | 4.9 |
| 21.1 | 4.2 | 16.1 |
| 21.4 | 4.1 | 100.0 |
| 22.3 | 4.0 | 29.8 |
| 22.8 | 3.9 | 12.8 |
| 23.1 | 3.9 | 23.9 |
| 23.8 | 3.7 | 7.3 |
| 24.0 | 3.7 | 4.7 |
| 24.6 | 3.6 | 0.3 |
| 25.1 | 3.5 | 1.8 |
| 25.9 | 3.4 | 3.2 |
| 26.6 | 3.4 | 7.8 |
| 27.0 | 3.3 | 14.6 |
| 27.4 | 3.3 | 8.9 |
| 28.2 | 3.2 | 4.7 |
| 28.5 | 3.1 | 3.1 |
| 28.9 | 3.1 | 1.3 |
| 29.6 | 3.0 | 1.6 |
| 29.6 | 3.0 | 2.8 |
| 29.9 | 3.0 | 2.4 |
| 30.3 | 2.9 | 2.7 |
| 31.0 | 2.9 | 0.9 |
| 31.6 | 2.8 | 2.0 |
| 31.9 | 2.8 | 4.2 |
| 32.5 | 2.8 | 1.2 |
| 33.0 | 2.7 | 2.3 |
| 34.0 | 2.6 | 2.3 |
| 34.3 | 2.6 | 1.4 |

Figure 2:
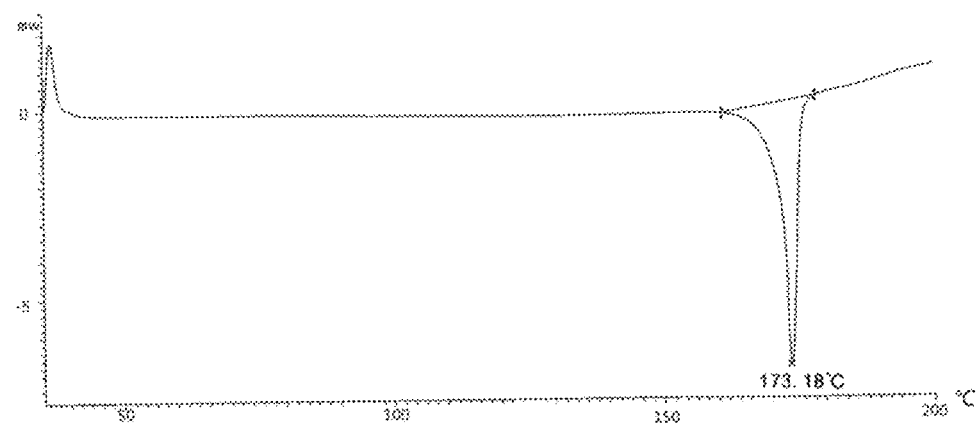
FIG. 2: a DSC graph of the crystalline form A of the compound of Formula (I).

The resulting sample was subjected to the DSC detection, and the DSC graph is as shown in FIG. 2, indicating the endothermic peak appeared at 173.18° C.

Figure 3:
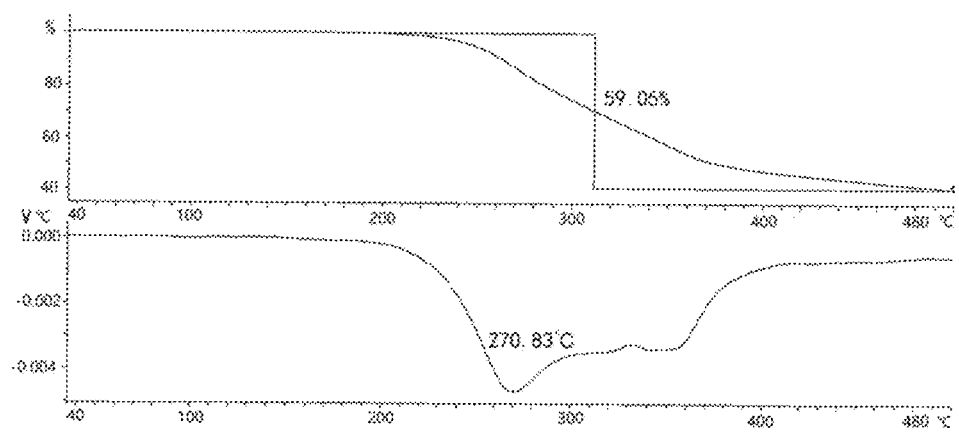
FIG. 3: a TGA graph of the crystalline form A of the compound of Formula (I).

The resulting sample was subjected to the TGA detection, and the TGA graph is as shown in FIG. 3, indicating the decomposition started at about 190° C.

Example 3: Preparation of the Crystalline Form a of the Compound of Formula (I)

The crystalline form A of the compound of Formula (I) was prepared according to a preparation method same as that in Example 2, wherein the methanol in Example 2 was replaced with a solvent in an amount as shown in Table 2 below. The resulting sample was subjected to XRPD detection, indicating the resulting product was the same as the crystalline form A obtained in Example 2.

TABLE 2

| Solvent | Ratio (Solute:Solvent) |
| --- | --- |
| ethanol | 30 mg/1.0 ml |
| n-propanol | 30 mg/1.5 ml |
| isopropanol | 30 mg/2.0 ml |
| n-butanol | 30 mg/2.7 ml |
| acetone | 30 mg/1.0 ml |
| butanone | 30 mg/1.0 ml |
| ethyl acetate | 30 mg/1.0 ml |
| isopropyl acetate | 30 mg/1.0 ml |
| butyl acetate | 30 mg/1.0 ml |
| dimethyl carbonate | 30 mg/1.0 ml |
| tetrahydrofuran | 30 mg/1.0 ml |
| dichloromethane | 30 mg/1.0 ml |
| chloroform | 30 mg/1.0 ml |
| acetonitrile | 30 mg/1.5 ml |
| methyl tert-butyl ether | 30 mg/1.5 ml |
| anisole | 30 mg/1.0 ml |
| toluene | 30 mg/1.5 ml |
| diethyl ether | 30 mg/1.5 ml |

Example 4: Preparation of the Crystalline Form A of the Compound of Formula (I)

The compound of Formula (I) prepared in Example 1 was dissolved in solvent A to obtain a solution comprising 30 mg/ml of the compound of Formula (I), followed by addition of solvent B in a volume equal to that of solvent A (the types and volume ratios of solvent A and solvent B are as shown in Table 3). The solution was allowed to stand at room temperature, the solvent was volatilized and removed, leading to the crystallization, and the solid was collected. XRPD detection indicated that the resulting crystalline form was the same as the crystalline form A of Example 2.

TABLE 3

| Solvent A (V) | Solvent B (V) | | | | | | |
| --- | --- | --- | --- | --- | --- | --- | --- |
| | methanol | Acetone | tetrahydrofuran | ethyl acetate | acetonitrile | toluene | dichloromethane |
| acetone | 1:1 | | | | | | |
| tetrahydrofuran | 1:1 | 1:1 | | | | | |
| ethyl acetate | 1:1 | 1:1 | 1:1 | | | | |
| acetonitrile | 1:1 | 1:1 | 1:1 | 1:1 | | | |
| toluene | 1:1 | 1:1 | 1:1 | 1:1 | 1:1 | | |
| dichloromethane | 1:1 | 1:1 | 1:1 | 1:1 | 1:1 | 1:1 | |
| water | 1:1 | 1:1 | 1:1 | / | 1:1 | / | / |
| methyl tert-butyl ether | / | 1:1 | 1:1 | 1:1 | 1:1 | 1:1 | 1:1 |

Example 5: Preparation of the Crystalline Form A of the Compound of Formula (I)

500 mg of the compound of Formula (I) prepared in Example 1 was weighed, and a certain amount of the solvent (the solvent types and addition ratios are shown in Table 4) was added thereto. The mixture was heated and stirred to form a clear solution, which was then slowly cooled to room temperature followed by filtration. The solid was collected, and XRPD detection indicated that the resulting crystalline form was the same as the crystalline form A of Example 2.

TABLE 4

| Solvent | Ratio (Solute:Solvent) |
| --- | --- |
| n-propanol | 0.5 g/4.0 ml |
| acetonitrile | 0.5 g/4.0 ml |
| diethyl ether | 0.5 g/30.0 ml |
| isopropanol | 0.5 g/4.0 ml |
| toluene | 0.5 g/4.0 ml |

Example 6: Conversion into a Crystalline Form from a Suspension of the Amorphous Form of the Compound of Formula (I)

50 mg of the compound of Formula (I) prepared in Example 1 was weighed, and then 0.5 ml of the solvent (the solvent types and addition ratios are shown in Table 5) was added thereto. The compound was dispersed and suspended, and then the mixture was stirred at room temperature under seal for 72 h followed by filtration. The solid was collected, and XRPD detection indicated that the resulting crystalline form was the same as the crystalline form A of Example 2.

TABLE 5

| Solvent | Ratio (Solute:Solvent) |
| --- | --- |
| ethanol | 50 mg/0.5 ml |
| n-propanol | 50 mg/0.5 ml |
| n-butanol | 50 mg/0.5 ml |
| n-hexane | 50 mg/2.0 ml |
| n-heptane | 50 mg/2.0 ml |
| cyclohexane | 50 mg/2.0 ml |
| acetonitrile | 50 mg/0.5 ml |
| diethyl ether | 50 mg/1.0 ml |
| methyl tert-butyl ether | 50 mg/0.5 ml |
| isopropyl ether | 50 mg/1.0 ml |
| toluene | 50 mg/0.5 ml |
| water | 50 mg/2.0 ml |
| petroleum ether | 50 mg/2.0 ml |

Example 7: Preparation of the Crystalline Form a of the Compound of Formula (I)

200 mg of the sample of the compound of Formula (I) prepared in Example 1 was weighed, and 4 ml of the solvent (the solvent types and addition ratios are shown in Table 6) was added thereto. The compound was dispersed and suspended, and then the mixture was stirred at 60° C. for 8 h followed by filtration. The solid was collected, and XRPD detection indicated that the resulting crystalline form was the same as the crystalline form A of Example 2.

TABLE 6

| Solvent | Ratio (Solute:Solvent) |
| --- | --- |
| n-hexane | 0.2 g/4.0 ml |
| cyclohexane | 0.2 g/4.0 ml |
| n-heptane | 0.2 g/4.0 ml |
| isopropyl ether | 0.2 g/4.0 ml |
| petroleum ether | 0.2 g/4.0 ml |
| Water | 0.2 g/4.0 ml |

Example 8: Conversion into a Crystalline Form from a Suspension of the Compound of Formula (I)

150 mg of the sample of the compound of Formula (I) prepared in Example 1 was weighed, and a suitable amount of the solvent (the solvent types and addition ratios are shown in Table 7) was added thereto. The compound was dispersed and suspended, and then the mixture was stirred at room temperature under seal for 72 h followed by filtration. The solid was collected, and XRPD detection indicated that the resulting crystalline form was the same as the crystalline form A of Example 2.

TABLE 7

| Solvent | Ratio (Solute:Solvent) |
| --- | --- |
| n-propanol | 150 mg/1.2 ml |
| n-hexane | 150 mg/3.0 ml |
| cyclohexane | 150 mg/3.0 ml |
| n-heptane | 150 mg/3.0 ml |
| acetonitrile | 150 mg/1.2 ml |
| methyl tert-butyl ether | 150 mg/1.2 ml |
| isopropyl ether | 150 mg/3.0 ml |
| Toluene | 150 mg/1.2 ml |
| Water | 150 mg/3.0 ml |
| petroleum ether | 150 mg/3.0 ml |
| diethyl ether | 150 mg/1.2 ml |
| n-butanol | 150 mg/1.7 ml |
| isopropanol | 150 mg/1.8 ml |
| ethanol | 150 mg/2.0 ml |

Example 9: Preparation of the Crystalline Form A of the Compound of Formula (I)

30 mg of the sample of the compound of Formula (I) prepared in Example 1 was weighed and placed in a penicillin bottle, and the open penicillin bottle was placed in a 50 ml beaker containing a suitable amount of the solvent (the types and amounts of the solvents are shown in Table 8). The beaker was sealed and allowed to stand at room temperature for about 8 days. The solid was collected, and XRPD detection indicated that the resulting crystalline form was the same as the crystalline form A of Example 2.

TABLE 8

| Solvent | Volume (ml) |
| --- | --- |
| methanol | 6 ml |
| Ethanol | 6 ml |
| isopropyl acetate | 6 ml |
| n-hexane | 6 ml |
| acetonitrile | 6 ml |

TABLE 8-continued

| Solvent | Volume (ml) |
| --- | --- |
| diethyl ether | 12 ml |
| methyl tert-butyl ether | 12 ml |
| Toluene | 6 ml |

Example 10: Preparation of an Amorphous Form of the Compound of Formula (I)

Figure 4:
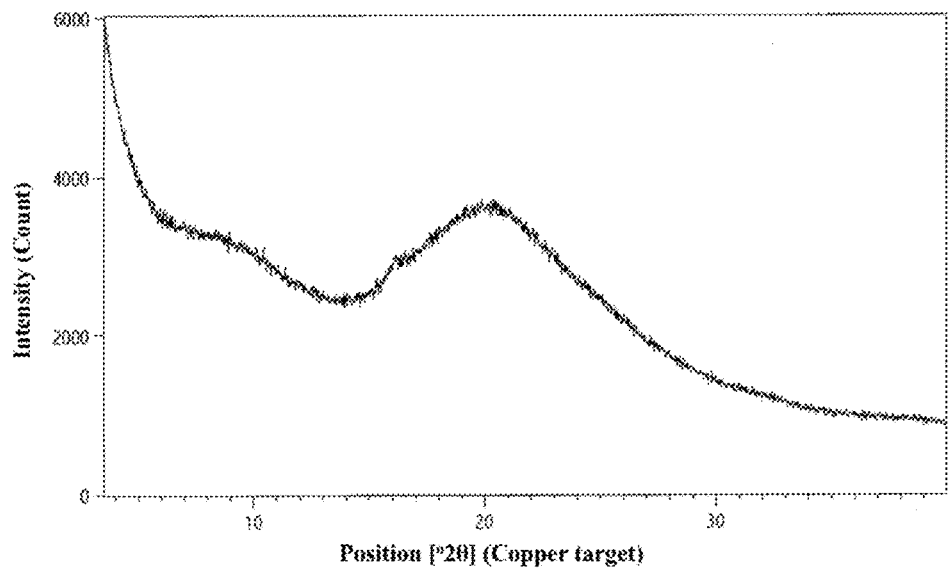
FIG. 4: an XRPD pattern of the amorphous form of the compound of Formula (I).

3 g of the sample of the compound of Formula (I) prepared in Example 1 was weighed, and 50 ml of the solvent (the solvent types and addition ratios are shown in Table 9) was added to form a clear solution. The solution was filtered, and then rotary evaporated under reduced pressure in a water bath at 45° C. with a rotary evaporator, to obtain a solid. The resulting sample was subjected to XRPD analysis, and the XRPD pattern is as shown in FIG. 4, indicating an amorphous form of the compound of Formula (I) was obtained.

TABLE 9

| Solvent | Ratio (Solute:Solvent) |
| --- | --- |
| dichloromethane | 3 g/50 ml |
| chloroform | 3 g/50 ml |

Experimental Example

Experimental Example 1. Study on the Stability of the Crystalline Form A at Room Temperature A sample of the crystalline form A of the compound of Formula (I) was allowed to stand at room temperature, and samples were taken on Day 5 and 15 for XRPD detection.

Test results: XRPD detection results showed that after standing at room temperature for 15 days, the crystalline form was the same as that in Example 2, and the crystalline form A did not change.

Experimental Example 2. Study on the Stability of the Crystalline Form A at a High Temperature A sample of the crystalline form A of the compound of Formula (I) was allowed to stand under vacuum at 60° C., and samples were taken on Day 2, 5 and 7, respectively, for XRPD detection.

Figure 6:
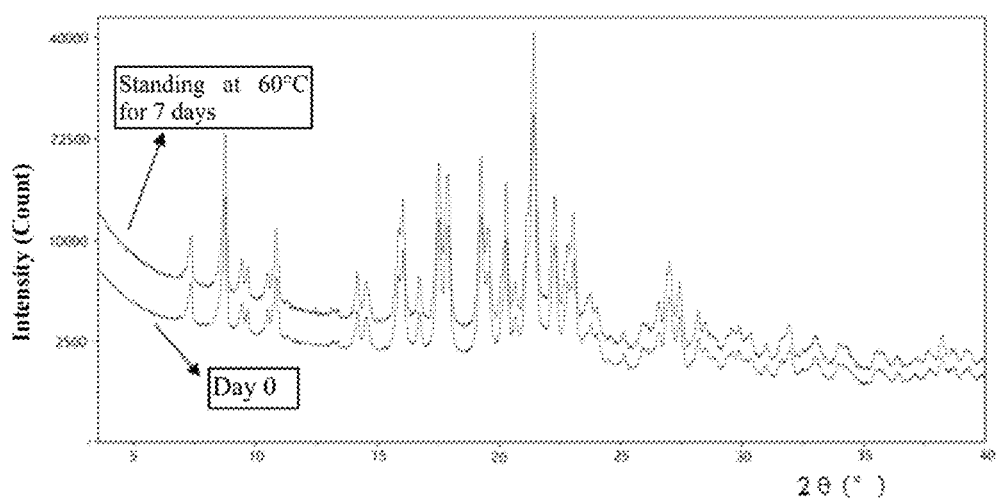
FIG. 6: an XRPD pattern comparison of the crystalline form A of the compound of Formula (I) after standing at 60° C. for 0 day and 7 days.

Test results: XRPD detection results showed that after standing under vacuum at 60° C. for 7 days, the crystalline form was the same as that in Example 2, and the crystalline form A did not change (an XRPD pattern comparison of the crystalline form A after standing at 60° C. for 0 day and 7 days is as shown in FIG. 6).

Experimental Example 3. Study on the Stability of the Crystalline Form A Under Grinding A sample of the crystalline form A of the compound of Formula (I) was ground at a constant speed in a mortar, and samples were taken after the grinding was performed for 2 and 5 minutes, respectively, for XRPD detection.

Test results: XRPD detection results showed that after being ground for 5 minutes, the crystalline form was the same as that in Example 2, and the crystalline form A did not change.

Experimental Example 4. DVS Study of the Crystalline Form A

The hygroscopicity of a sample of the crystalline form A of the compound of Formula (I) was measured through dynamic vapor sorption (DVS): the hygroscopicity thereof was measured at 25° C., 10% humidity gradient in the range of 0%-90%-0%.

Figure 5:
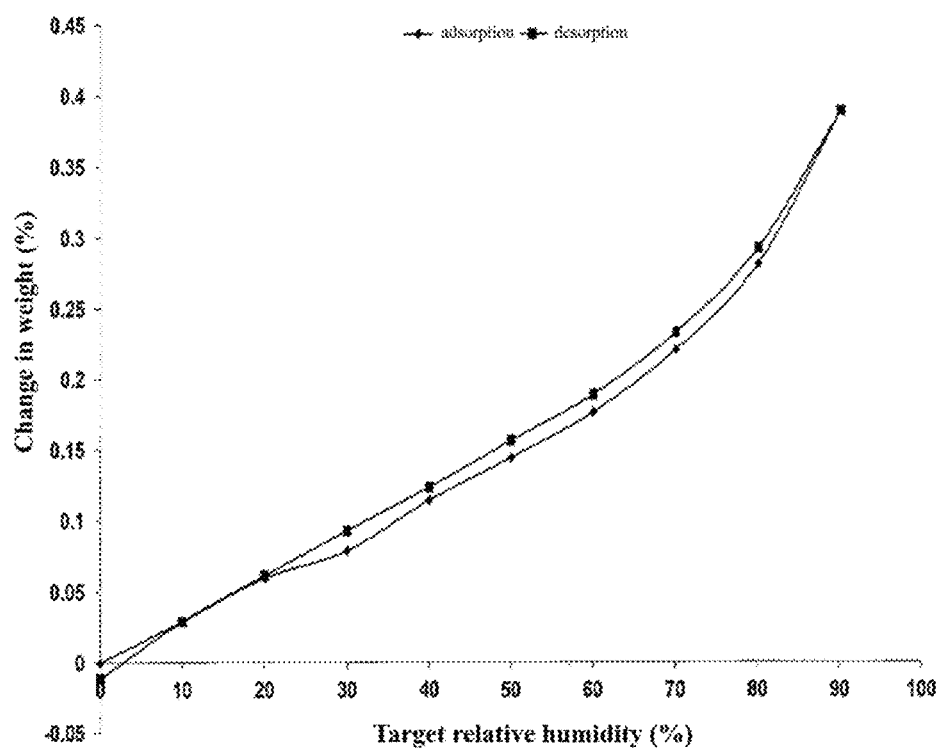
FIG. 5: a DVS graph of the crystalline form A of the compound of Formula (I).

The DVS graph is as shown in FIG. 5, and the results showed that the weight increase by hygroscopy of the sample was 0.28% under the condition of 80% humidity. According to the 2015 edition of the Chinese Pharmacopoeia, a substance having a weight increase by hygroscopy within the range of 0.2%-2% belongs to "slightly hygroscopic" substances.

Experimental Example 5. Pharmacokinetic Experiment of the Crystalline Form A in Rats 1. Test Sample Formulation of the test sample for intravenous administration: the sample of Example 5 (the solvent used in the crystal preparation was isopropanol) was taken and dissolved in 5% DMSO+5% Solutol (HS15)+90% normal saline, to obtain the test sample solution for intravenous administration;

Formulation of the test sample for intragastric administration: the sample of Example 5 (the solvent used in the crystal preparation was isopropanol) was taken and suspended in 97.5% of 0.5% methyl cellulose (MC)+2.5% Solutol (HS15) to obtain a suspension, which was used as the test sample for intragastric administration.

2. Test Method and Results

12 SD rats were randomly divided into two groups, groups A and B (6 rats per group, half male and half female). The rats in Group A were each given a single intravenous injection of the sample drug; the rats in Group B were each given the sample drug through intragastric administration, and the dosages are both 3 mg/kg. The blood sampling time points for the intravenous and intragastric administration were before administration and 0.083, 0.25, 0.5, 1.0, 2.0, 4.0, 6.0, 8.0, 10, and 24 h after administration. The pharmacokinetic parameters were calculated according to the blood drug concentration, and the results are shown in Table 10. According to the data in Table 10, the absolute bioavailability of the crystalline form A in rats was 62.4% (calculated based on $AUC_{0-\infty}$), indicating good oral absorption in rats.

Experimental Example 6. Safety Experiment of the Crystalline Form A of the Compound of Formula (I)

Formulation of the test sample: a required amount of a sample of the crystalline form A of Example 5 (the solvent used in the crystal preparation was isopropanol) was weighed and added to a mortar, polyethylene glycol-15 hydroxystearate (HS15) in an amount of 2.5% of the total volume was added, and the sample was evenly ground. The mortar was washed with a 0.5% methyl cellulose (MC) solution with grinding, until there was no visible residue. The mixture was transferred to a calibrated container, and then diluted with a 0.5% methyl cellulose solution to the volume. The solution was stirred uniformly with a magnetic stirrer to obtain a suspension, which was used as the test sample.

1. Single-Dose Toxicity in SD Rats 4 groups (10 rats per group, half male and half female) were set in the single-dose toxicity test in SD rats, and they were the vehicle control group and the low-, medium-, and high-dose groups of the crystalline form A of the compound of Formula (I), respectively. After intragastric administration, the rats were observed for 14 days. During the observation period, it was found that the animals were in good condition, there were no significant changes in body weight and food intake, the hematology and blood biochemical indicators were normal, and no abnormalities were observed in gross anatomy. At the end of the test, the crystalline form A of the compound of Formula (I) was well tolerated by the SD rats under the conditions in the present test, and no abnormalities were observed after 14 days of administration.

2. Single Dose Toxicity in Beagle Dogs 3 groups (4 dogs per group, half male and half female) were set in the single-dose toxicity test in Beagle dogs, and they were the vehicle control group and the low- and high-dose groups of the crystalline form A of the compound of Formula (I). After intragastric administration, the dogs in each group were observed for 14 days. During the observation period, it was found that the animals were in good condition, there were no significant changes in body weight, the hematology and blood biochemical indicators were normal, there were no obvious abnormalities in lead II electrocardiogram, respiratory rate and blood pressure, and no abnormalities were observed in gross anatomy.

The test results showed that the single dose of the crystalline form A of the compound of Formula (I) was well tolerated by the Beagle dogs, and no abnormalities were observed after 14 days of administration.

Experimental Example 7. Determination of the Solubility of the Crystalline Form A Test solvents: methanol, acetonitrile, ethanol, isopropanol, a 0.1 mol/L aqueous solution of hydrochloric acid and a 0.1 mol/L aqueous solution of sodium hydroxide.

TABLE 10

Pharmacokinetic parameters after single administration of the crystalline form A in rats (n = 6, half male and half female)

| mode of administration | $AUC_{0-t}$ (µg · h/ml) | $AUC_{0-\infty}$ (µg · h/ml) | $C_{max}$ (µg/ml) | $t_{1/2}$ (h) | $T_{max}$ (h) |
|---|---|---|---|---|---|
| intravenous | 10.4 ± 4.5 | 10.4 ± 4.5 | 9.21 ± 2.10 | 0.88 ± 0.18 | / |
| intragastric | 6.46 ± 2.94 | 6.49 ± 2.95 | 3.98 ± 1.44 | 1.01 ± 0.26 | 0.38 (0.25-0.5) |

Note:
$T_{max}$ value is the median (range).

Test method: the investigation was conducted according to Item 15(2) of the General Notices in Volume IV of the Chinese Pharmacopoeia (2015 edition). An appropriate amount of a sample of the crystalline form A prepared in Example 5 (the solvent used in the crystal preparation was isopropanol) was weighed and added to a certain volume of the solvent at 25±2° C. The mixture was shaken strongly for 30 seconds at an interval of 5 minutes. The solubility behavior was observed for 30 minutes. It was considered to be completely soluble if none of the particles of the solute was observed.

Test results: the sample of the crystalline form A was soluble in methanol, acetonitrile and ethanol, slightly soluble in isopropanol, and sparingly soluble in a 0.1 mol/L aqueous solution of hydrochloric acid and a 0.1 mol/L aqueous solution of sodium hydroxide Experimental Example 8. Determination of the log P Value of the Crystalline Form A The log P value of a sample of the crystalline form A prepared in Example 5 (the solvent used in the crystal preparation was isopropanol) was measured with the Sirius T3 instrument for physical and chemical profile determination. The Sirius log P test method (pH-metric medium log P) was employed, wherein the pH-metric medium log P determination mode was selected, and the titration order was from low to high pH.

Test results: the log P value of the product was 2.4-2.6. This indicates that the crystalline form A of the present invention has excellent membrane permeability, which is beneficial to the ADME process and receptor affinity in vivo.

The solid form of the compound of Formula (I) and the preparation method thereof disclosed in the present application can be realized by those skilled in the art by referring to the disclosures herein together with appropriate modifications to the raw materials, and process parameters etc. The methods and products of the present application have been described in the optimal examples. It is obvious to those skilled in the art that the technology of the present invention can be realized by modification or appropriate amendment and combination of the methods and products described herein without departing from the content, spirit and scope of the invention. It is particularly important to note that all similar replacements and modifications are obvious to those skilled in the art and are considered to be included in the spirit, scope and content of the present invention.

What is claimed is:

1. A crystalline form A of the compound of Formula (I) characterized in that the X-ray powder diffraction pattern of the crystalline form A has characteristic peaks at diffraction angles of 8.7±0.2°, 17.5±0.2°, 19.3±0.2°, 20.3±0.2° and 21.4±0.2°,

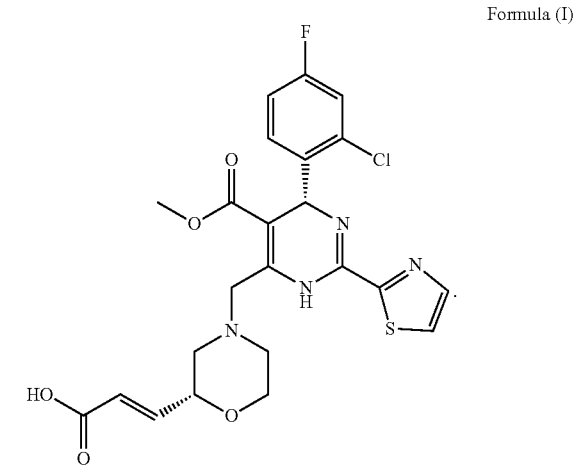 [SMILES: COC(=O)C1=C(CN2CCO[C@H](/C=C/C(=O)O)C2)NC(c2nccs2)=N[C@H]1c1ccc(F)cc1Cl]

Formula (I)

2. The crystalline form A according to claim 1, further comprising peaks at diffraction angles of 16.0±0.2°, 17.8±0.2°, 22.3±0.2° and 23.1±0.2°.

3. The crystalline form A according to claim 1, characterized in that the endothermic peak in a differential scanning calorimetry (DSC) graph of the crystalline form A of the compound of Formula (I) appears at 173±2° C.

4. The crystalline form A according to claim 1, characterized in that the crystalline form A of the compound of Formula (I) starts to decompose at 190±2° C. measured using thermogravimetric analysis (TGA).

5. A pharmaceutical composition comprising the crystalline form A according to claim 1, and one or more pharmaceutically acceptable carriers or one or more additional therapeutic agents.

6. A pharmaceutical formulation comprising the crystalline form A according to claim 1, and one or more pharmaceutically acceptable carriers.

7. The crystalline form A according to claim 2, wherein the X-ray powder diffraction pattern of the crystalline form A is as shown in FIG. 1.

8. The crystalline form A according to claim 3, wherein the DSC graph of the crystalline form A is as shown in FIG. 2.

9. The crystalline form A according to claim 4, wherein the TGA graph of the crystalline form A is as shown in FIG. 3.

* * * * *